United States Patent
Dolbier, Jr. et al.

(10) Patent No.: US 6,284,933 B1
(45) Date of Patent: *Sep. 4, 2001

(54) TFPX SYNTHESIS

(76) Inventors: William R. Dolbier, Jr., 8205 SW. 39th Pl., Gainesville, FL (US) 32608; Xiao X. Rong, 328 SW. 34th St., Gainesville, FL (US) 32602; Walter E. Stalzer, 6211 Chase Dr., Mentor, OH (US) 44060

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/761,216

(22) Filed: Dec. 6, 1996

Related U.S. Application Data

(63) Continuation of application No. 08/735,726, filed on Oct. 23, 1996, now abandoned.

(51) Int. Cl.$^7$ .................................................. C07C 22/00
(52) U.S. Cl. ................................................ 570/145
(58) Field of Search ................................. 570/145

(56) References Cited

FOREIGN PATENT DOCUMENTS

0293937 * 12/1986 (JP) ...................................... 570/145

* cited by examiner

Primary Examiner—Alan Siegel

(57) ABSTRACT

A method of making TFPX using an $S_N2$ type nucleophilic displacement reaction. The method includes reacting a nucleophilic fluorine molecule with a nonfluorinated-tetrahalo-p-xylene molecule. Exemplary nucleophilic fluorine molecules include, but are not limited to, CsF, KF, NaF and LiF. The nonfluorinated-tetrahalo-p-xylene molecules may include, α,α,α',α'-tetrachloro-p-xylene, α,α,α',α'-tetrabromo-p-xylene or α,α,α',α'-tetraiodo-p-xylene. The reaction may be carried out in an open or closed container. Furthermore, the reaction may be carried out in the presence of a phase transfer catalyst. In certain embodiments, the reaction is carried in a substantially solvent-free environment.

25 Claims, No Drawings

TFPX SYNTHESIS

CROSS-REFERENCE TO RELATED APPLICATION

The present application is a continuation application of U.S. patent application Ser. No. 08/735,726, filed Oct. 23, 1996, entitled TFPX Synthesis now abandoned.

BACKGROUND OF THE INVENTION

1. Field of the Invention

The present invention relates generally to methods of synthesizing TFPX, and more specifically to such methods which utilize $S_N2$ nucleophilic substitution reactions.

2. Discussion of the Related Art

Dielectric films are widely used throughout both the electronics and coatings industries. Due to their relatively high dielectric constants and melting points, there is an increasing interest in forming dielectric layers from parylene polymers having the molecular structure:

wherein X is typically a hydrogen atom or a fluorine atom.

Parylene polymers are usually formed by chemical vapor deposition processes. One such process is the Gorham process in which a parylene dimer having the molecular structure:

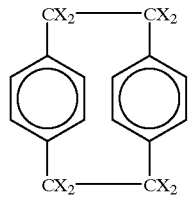

is vaporized and the dimer bonds are then cleaved to yield parylene monomers. The parylene monomers are deposited onto a surface and subsequently polymerized. Because the dielectric constant and melting temperature of parylene polymers usually increases as the number of fluorine atoms within the polymer increases, it is desirable to use octafluoro-[2,2]paracyclophane (hereinafter "AF4") having the molecular structure:

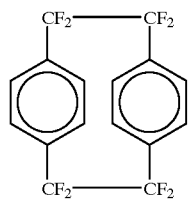

as the parylene dimer. α,α,α',α'-tetrafluoro-p-xylene (hereinafter "TFPX") having the molecular structure:

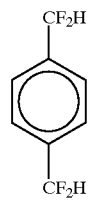

is often used as the starting material in AF4 synthesis. The conventional procedure for synthesizing TFPX involves the fluorination of terephthaldehyde, which has the molecular structure:

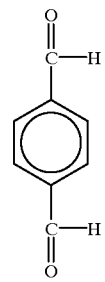

$SF_4$ and $MoF_6$ are the most commonly used reagents for terephthaldehyde fluorination. However, $SF_4$ and $MoF_6$ are expensive, reducing the industrial utility of this synthetic scheme. In addition, $SF_4$ and $MoF_6$ are toxic materials, so a large amount of hazardous waste is produced using these reagents.

Russian Patent No. 2,032,654 discloses an alternate method of synthesizing TFPX in which α,α,α',α'-tetrabromo-p-xylene (hereinafter "TBPX") having the molecular structure:

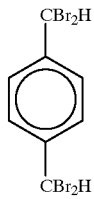

is reacted with $SbF_3$ to produce TFPX. This method employs the well established electrophilic catalyzed $S_N1$ reaction mechanism for replacement of benzylic halogen atoms of the TBPX with fluorine atoms. According to this method, the antimony atom in $SbF_3$ acts as an electrophile which removes bromine from TBPX to form a carbocation. The carbocation subsequently reacts with fluorine to form TFPX. While this reaction is reported to provide a good yield when carried out under comparatively mild reaction conditions, antimony containing compounds are highly toxic and expensive. Furthermore, the $SbF_3$ is used in a stoichiometric amount rather than a catalytic amount, resulting in large quantities of hazardous waste materials. Therefore, this method of synthesizing TFPX has limited use for industrial applications.

Therefore, it remains a challenge in the art to synthesize TFPX using a method that is comparatively inexpensive and results in a reduced amount of hazardous waste.

SUMMARY OF THE INVENTION

Accordingly, it is an object of the present invention to provide a method of synthesizing TFPX that results in reduced amounts of hazardous waste.

It is another object of the present invention to provide such a method that utilizes reagents that are comparatively nontoxic.

In one illustrative embodiment, the present invention provides a method of synthesizing TFPX. This method includes reacting a nonfluorinated tetrahalo-p-xylene compound with a nucleophilic fluorine molecule.

In another illustrative embodiment of the present invention, the method of synthesizing TFPX includes reacting α,α,α',α'-tetrachloro-p-xylene with CsF.

In a further illustrative embodiment of the present invention, the method of synthesizing TFPX includes reacting α,α,α',α'-tetrachloro-p-xylene with KF.

DETAILED DESCRIPTION

The present invention relates to the synthesis of TFPX by the reaction of nucleophilic fluorine molecules with nonfluorinated tetrahalo-p-xylenes via $S_N2$ type nucleophilic displacement reactions. According to this synthetic scheme, the benzylic halogen atoms of a nonfluorinated tetrahalo-p-xylene are replaced by the fluorine atoms in a nucleophilic fluorine molecule without formation of a carbocation intermediate. This result is unexpected because the conventional approach to the displacement of benzylic halogen atoms involves electrophilically catalyzed $S_N1$ reaction mechanisms (i.e., the formation of carbocation intermediates).

A "nucleophilic fluorine molecule" as used herein refers to a molecule that donates a pair of electrons to an atomic nucleus by the addition of a fluorine atom to the atomic nucleus. According to the present invention, nucleophilic fluorine molecules should be chemically stable under TFPX synthesis reaction conditions as described below. Such nucleophilic fluorine molecules include, for example, CsF, NaF, KF, LiF and $CaF_2$. Preferably, the nucleophilic fluorine molecule is CsF or KF. While certain nucleophilic fluorine molecules have been disclosed herein, other nucleophilic fluorine molecules appropriate for use in the present invention will be apparent to those skilled in the art.

As used herein, the term "nonfluorinated tetrahalo-p-xylene" denotes a molecule having the structure:

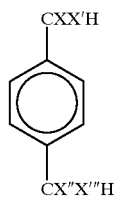

wherein X, X', X" and X'" are benzylic halogen atoms that may each be a chlorine atom, a bromine atom or an iodine atom. An exemplary and nonlimiting list of nonfluorinated tetrahalo-p-xylenes includes α,α,α',α'-tetraiodo-p-xylene (hereinafter "TIPX") having the molecular structure:

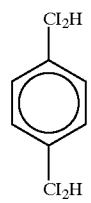

α,α,α',α'-tetrachloro-p-xylene (hereinafter "TCPX") having the molecular structure:

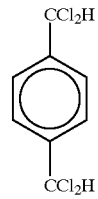

and TFBX. In a preferred embodiment, the nonfluorinated tetrahalo-p-xylene is TCPX.

By "benzylic halogen" it is herein meant to refer to a halogen atom that is bonded to a carbon atom that is directly bonded to a benzene ring (i.e., alpha to a benzene ring). For example, in the molecular structure:

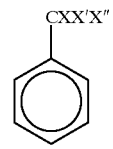

X, X' and X" are each benzylic halogen atoms.

In certain embodiments, the $S_N2$ type nucleophilic displacement reactions of the present invention may be performed in a solvent system. These solvents are generally aprotic polar solvents, such as dimethyl formamide (DMF) or dimethyl sulfoxide (DMSO). Other solvents appropriate for use in the present invention will be apparent to those skilled in the art and are intended to be within the scope of the present invention.

In alternate embodiments, TFPX synthesis may be carried out under conditions that are substantially free from any solvents (i.e., conditions under which the reaction mixture includes less than 0.5% solvent by weight). By making TFPX in a substantially solvent free environment, the increased costs associated with the use of solvents (e.g., for separation of solvents from product and solvent disposal) can be avoided.

Typically, substantially no volatile products are formed during TFPX synthesis, so the pressure of the reaction vessel does not normally increase during the reaction. As a result, TFPX may be synthesized using open systems or closed systems. For example, in some embodiments, TFPX synthesis may be performed in standard laboratory containers such as, for example, three-necked flasks. In other embodiments, TFPX may be made using a closed container, such as an autoclave or a low pressure bottle system (e.g., a parr) which is held at a few atmospheres pressure. Furthermore, to provide compatibility with certain industrial settings, the reaction may be scaled up and run at pressures of about 1.5 atmospheres.

The temperature at which TFPX is synthesized depends upon the reactants and the reaction conditions. For example, by varying the nucleophilic fluorine molecule and/or the nonfluorinated tetrahalo-p-xylene molecule, the reaction temperature may be increased or decreased. Furthermore, the temperature is generally lower when the reaction is carried out in a closed system compared to an open system. In embodiments in which TFPX is synthesized using a solvent, the temperature of the reaction mixture should be high enough to cause TFPX formation. However, if the reaction temperature is too high, undesirable side reactions that cause polymerization or elimination reactions that form tarry materials may occur. Thus, the reaction mixture is ideally maintained at a temperature high enough to form TFPX without resulting in these side reactions. When TFPX is made in a substantially solvent free environment, the temperature of the reaction mixture should be also be high enough to form TFPX without resulting in unwanted side reactions. In certain embodiments, it may be advantageous to use a reaction temperature high enough to melt the nonfluorinated tetrahalo-p-xylene such that the reaction occurs in one phase.

According to the present invention, the reaction mixture should be held at a temperature of from about 180° C. to about 220° C. for CsF, from about 280° C. to about 300° C. for KF and from about 280° C. to about 300° C. for NaF.

To increase the reaction rate, some embodiments of the $S_N2$ type nucleophilic displacement reactions of the present invention may be carried out in the presence of a phase transfer catalyst. Phase transfer catalysts appropriate for use in the present invention should be capable of enhancing the rate of TFPX formation without increasing the relative rate or amount of unwanted byproducts. In addition, phase transfer catalysts should be stable under the reaction conditions used in TFPX synthesis. One example of such a phase transfer catalyst is tetraphenyl phosphonium chloride. In addition, it is to appreciated that, in some embodiments, TFPX may be synthesized in a substantially phase transfer catalyst free environment (i.e., under conditions where there is less than about 0.5% by weight phase transfer catalyst in the reaction mixture).

The following examples are intended to be illustrative only and should not be construed as limiting.

EXAMPLE I

TCPX was synthesized as follows. About 850 grams of p-xylene and about 26.6 grams of triphenyl phosphate were added to a 2 liter flask. The p-xylene and triphenyl phosphate were mixed vigorously, held at a temperature of from about 75° C. to about 80° C. and exposed to radiation from a 500 Watt mercury lamp held about 6 centimeters from the sample while chlorine gas was bubbled through the mixture. After 110 hours about 4.2 equivalents of chlorine were reacted to form a product mixture, and the reaction was terminated. Nitrogen gas was bubbled through the product mixture for about 20 minutes, and this mixture was then poured into a hot isopropanol alcohol bath having about 20 grams of activated carbon. The resulting solution was filtered and cooled to allow a precipitate to form. This precipitate was filtered from the solution to obtain about 650 grams of TCPX in the form of colorless crystals with a melting point of about 89° C. to about 91° C. The TCPX had a purity of about 94%. The major impurity was α,α,α'-trichloro-p-xylene (about 5% by weight), and the minor impurity was α,α,α,α',α'-pentachloro-p-xylene (about 1% by weight).

EXAMPLE II

About 300 grams of CsF (purchased from CM Chemical Products, Inc., located in Berkeley Heights, N.J.) and about 100 grams of TCPX (synthesized as described in Example I) were added to a 500 mL three-necked flask. This mixture resulted in a molar ratio of CsF:TCPX of about 4.8:1. The CsF and TCPX were thoroughly mixed and heated to about 180° C. At this temperature, the TCPX melted and a slurry of TCPX and CsF was formed. This slurry was held at about 180° C. and stirred for about eight hours. The liquid phase was then distilled from the flask at a an aspirator pressure of from about 15 to about 20 mm Hg. Gas chromatographic analysis of the distillate was performed using an HP 5890 Series 2 gas chromatatograph from Hewlett-Packard with a ten foot packed column having SE-30 as the liquid phase. This analysis indicated a clean conversion of TCPX to TFPX with a yield of about 80% (i.e., about 58 grams of TFPX were made).

EXAMPLE III

About 150 grams of KF (purchased from Aldrich Chemical, located in Milwaukee, WI) and about 75 grams of TCPX (synthesized as described in Example I) were added to a 500 mL three-necked flask. This mixture resulted in a molar ratio of KF:TCPX of about 8:1. The KF and TCPX were thoroughly mixed and heated to about 280° C. At this temperature, the TCPX melted and a slurry of TCPX and KF was formed. This slurry was held at about 280° C. and stirred for about twelve hours. The liquid phase was then distilled from the flask as described in Example II. Gas chromatographic analysis of the distillate indicated a clean conversion of TCPX to TFPX with a yield of about 90% (i.e., about 45 grams of TFPX were made).

EXAMPLE IV

About 150 grams of KF and about 75 grams of TCPX (synthesized as described in Example I) were thoroughly mixed and then added to a 600 mL autoclave. This mixture resulted in a molar ratio of KF:TCPX of about 8:1. This mixture was heated to a temperature range of from about 260° C. to about 270° C. In this temperature range, the TCPX melted and a slurry of TCPX and KF was formed. This slurry was held in this temperature range for about twelve hours. The liquid phase was then distilled from the flask as described in Example II. Gas chromatographic analysis of the distillate indicated a clean conversion of TCPX to TFPX with a ield of about 87% (i.e., about 43 grams of TFPX).

EXAMPLE V

About 150 grams of NaF (Aldrich Chemical) and about 75 grams of TCPX (synthesized as described in Example I) were added to a 500 mL three-necked flask. This mixture resulted in a molar ratio of NaF:TCPX of about 11:1. The NaF and TCPX were thoroughly mixed and heated to about 280° C. At this temperature, the TCPX melted and a slurry of TCPX and NaF was formed. This slurry was held at about 280° C. and stirred for about twelve hours. The liquid phase was then distilled from the flask as described in Example II. Gas chromatographic analysis of the distillate indicated incomplete exchange after twelve hours.

EXAMPLE VI

About 150 grams of NaF and about 75 grams of TCPX (synthesized as described in Example I) were thoroughly mixed and then added to a 600 mL autoclave. This mixture resulted in a molar ratio of NaF:TCPX of about 11:1. This mixture was heated to a temperature range of from about 260° C. to about 270° C. In this temperature range, the TCPX melted and a slurry of TCPX and NaF was formed. This slurry was held in this temperature range for about twelve hours. The liquid phase was then distilled from the flask as described in Example II. Gas chromatographic analysis of the distillate indicated a conversion of TCPX to TFPX with a purity of 65% and a yield of about 45%. The portion of the distillate that was not TCPX corresponded to partially-fluorinated compounds.

Having thus described certain embodiments of the present invention, various alterations, modifications and improvements will be apparent to those skilled in the art. Such alterations, modification and improvements are intended to be within the spirit and scope of the present invention. Accordingly, the foregoing disclosure is by way of example only and is not intended to be limiting. The present invention is limited only by the following claims and equivalents thereto.

What is claimed is:

1. A method of synthesizing TFPX, the method comprising the steps of:

reacting a nucleophilic fluorine molecule comprising a fluoride of a Group IA or Group IIA metal with a nonfluorinated tetrahalo-p-xylene molecule to synthesize the TFPX via an $S_N2$-type nucleophilic displacement reaction in a substantially solvent-free environment at a temperature of at least about 180° C., and wherein the reacting step is performed with a molar ratio of the nucleophilic fluorine molecule to the nonfluorinated tetrahalo-p-xylene compound of about 4 to 1.

2. The method according to claim 1, wherein the reacting step includes reacting CsF with the nonfluorinated tetrahalo-p-xylene molecule.

3. The method according to claim 1, wherein the reacting step includes reacting NaF with the nonfluorinated tetrahalo-p-xylene molecule.

4. The method according to claim 1, wherein the reacting step includes reacting KF with the nonfluorinated tetrahalo-p-xylene molecule.

5. The method according to claim 1, wherein the reacting step includes reacting LiF with the nonfluorinated tetrahalo-p-xylene molecule.

6. The method according to claim 1, wherein the reacting step includes reacting the nucleophilic fluorine molecule with TCPX.

7. The method according to claim 1, wherein the reacting step includes reacting the nucleophilic fluorine molecule with TBPX.

8. The method according to claim 1, wherein the reacting step includes reacting the nucleophilic fluorine molecule with TIPX.

9. The method according to claim 1, wherein the reacting step is performed at a temperature of at least about 280° C.

10. The method according to claim 1, wherein the reacting step is performed with a molar ratio of the nucleophilic fluorine molecule to the nonfluorinated tetrahalo-p-xylene compound of greater than about 4 to 1.

11. The method according to claim 1, wherein the reacting steps includes reacting the nucleophilic fluorine molecule and the nonfluorinated tetrahalo-p-xylene molecule in a mixture that includes a phase transfer catalyst.

12. The method according to claim 1, wherein the reacting steps includes reacting the nucleophilic fluorine molecule and the nonfluorinated tetrahalo-p-xylene molecule in a mixture that is substantially free of any phase transfer catalysts.

13. A method of synthesizing TFPX, the method comprising the step of:

reacting a nucleophilic fluorine molecule comprising a fluoride of a Group IA or Group IIA metal with TCPX to synthesize the TFPX via an $S_N2$-type nucleophilic displacement reaction at a temperature of at least about 180° C., and wherein the reacting step is performed with a molar ratio of the nucleophilic fluorine molecule to the nonfluorinated tetrahalo-p-xlene compound of at least about 4 to 1.

14. The method according to claim 13, wherein the reacting step includes reacting CsF with the TCPX.

15. The method according to claim 13, wherein the reacting step is performed in an open container.

16. The method according to claim 13, wherein the reacting step is performed in a closed container.

17. The method according to claim 16, wherein the reacting step is performed at a temperature of about 160° C.

18. The method according to claim 13, wherein the reacting step includes reacting KF with the TCPX.

19. The method according to claim 18, wherein the reacting step is performed with a molar ratio of the KF to the TCPX of about 8 to 1.

20. The method according to claim 19, wherein the reacting step is performed in an open container.

21. The method according to claim 20, wherein the reacting step is performed at a temperature of about 280° C.

22. The method according to claim 19, wherein the reacting step is performed in a closed container.

23. The method according to claim 16, wherein the reacting step is performed at a temperature of about 260° C.

24. The method according to claim 6, further comprising the steps of:

mixing p-xylene and triphenyl phosphate at a temperature of from about 75° C. to about 80° C. to form a first mixture;

exposing the first mixture to radiation from a mercury lamp while bubbling chlorine gas through the mixture to form a product;

bubbling nitrogen gas through the product;

pouring the product on an isopropanol bath containing activated carbon to form a second mixture;

cooling the second mixture; and filtering the second mixture to form the TCPX.

25. A method of synthesizing TFPX, the method comprising the steps of:

reacting a potassium fluoride molecule with TCPX to synthesize the TFPX via an $S_N2$-type nucleophilic displacement reaction at a temperature of at least about 280° C., and wherein the reacting step is performed with a molar ratio of the nucleophilic fluorine molecule to the nonfluorinated tetrahalo-p-xylene compound of about 8 to 1.

* * * * *